(12) United States Patent
Ge et al.

(10) Patent No.: US 10,786,171 B2
(45) Date of Patent: Sep. 29, 2020

(54) MEMRISTOR CODE COMPARATOR TO COMPARE SENSOR SIGNALS TO REFERENCE SIGNALS

(71) Applicant: Hewlett-Packard Development Company, L.P., Spring, TX (US)

(72) Inventors: Ning Ge, Palo Alto, CA (US); Ralph A. Morales, Palo Alto, CA (US); Terrance J. OShea, Vancouver, WA (US); Helen A. Holder, Palo Alto, CA (US); David George, Palo Alto, CA (US); Hafid Hamadene, Palo Alto, CA (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 0 days.

(21) Appl. No.: 16/343,865

(22) PCT Filed: Oct. 25, 2016

(86) PCT No.: PCT/US2016/058666
§ 371 (c)(1),
(2) Date: Apr. 22, 2019

(87) PCT Pub. No.: WO2018/080451
PCT Pub. Date: May 3, 2018

(65) Prior Publication Data
US 2019/0261884 A1    Aug. 29, 2019

(51) Int. Cl.
*A61B 5/04*        (2006.01)
*A61B 5/0432*     (2006.01)
(Continued)

(52) U.S. Cl.
CPC ...... *A61B 5/04325* (2013.01); *A61B 5/04012* (2013.01); *A61B 5/04085* (2013.01);
(Continued)

(58) Field of Classification Search
CPC ............ A61B 5/04012; A61B 5/04085; A61B 5/04325; A61B 5/7221; G11C 13/0026;
(Continued)

(56) References Cited

U.S. PATENT DOCUMENTS 7,558,622 B2    7/2009 Tran
7,902,867 B2 *  3/2011 Mouttet ............. G11C 13/0002
                                                  326/41
(Continued)

FOREIGN PATENT DOCUMENTS

WO    WO-2015150199 A1    10/2015
WO    WO-2016068739 A1    5/2016
WO    WO-2016151445 A1    9/2016

OTHER PUBLICATIONS

Hu, F. et al.; Low-power, Intelligent Sensor Hardware Interface for Medical Data Preprocessing; Jul. 2009.

*Primary Examiner* — Vanthu T Nguyen
(74) *Attorney, Agent, or Firm* — Dicke Billig & Czaja PLLC

(57) ABSTRACT

One example of a device includes a sensor, a memristor code comparator, and a controller. The sensor is to provide a sensor signal. The memristor code comparator is to compare the sensor signal to a reference signal. The controller is to determine a status of the sensor signal based on the comparison.

20 Claims, 5 Drawing Sheets

(51) Int. Cl.
*A61B 5/0408* (2006.01)
*G11C 13/00* (2006.01)
*A61B 5/00* (2006.01)

(52) U.S. Cl.
CPC .......... *A61B 5/7221* (2013.01); *G11C 13/004* (2013.01); *G11C 13/0026* (2013.01); *G11C 13/0028* (2013.01); *G11C 13/0069* (2013.01); *G11C 2013/0054* (2013.01); *G11C 2213/77* (2013.01)

(58) Field of Classification Search
CPC .............. G11C 13/0028; G11C 13/004; G11C 13/0069; G11C 2013/0054; G11C 2213/77
See application file for complete search history.

(56) References Cited

U.S. PATENT DOCUMENTS

| | | | |
|---|---|---|---|
| 9,489,618 B2* | 11/2016 | Roy | G11C 11/161 |
| 2013/0132314 A1* | 5/2013 | Snider | G06N 3/063 |
| | | | 706/15 |
| 2014/0028347 A1* | 1/2014 | Robinett | G11C 13/0007 |
| | | | 326/38 |
| 2015/0248833 A1 | 9/2015 | Arne et al. | |
| 2015/0257647 A1 | 9/2015 | Buck et al. | |
| 2016/0045135 A1 | 2/2016 | Kim et al. | |
| 2016/0174908 A1* | 6/2016 | Nair | A61B 5/742 |
| | | | 600/301 |

* cited by examiner

MEMRISTOR CODE COMPARATOR TO COMPARE SENSOR SIGNALS TO REFERENCE SIGNALS

BACKGROUND

Wearable devices (e.g., fitness trackers, medical devices, etc.) and Internet of Things (IoT) devices (e.g., smart home devices, environmental monitoring devices, security devices, etc.) are often powered by batteries, energy storage devices, or energy harvesting devices. Many wearable devices and IoT devices include sensors that provide signals to be recorded and/or analyzed by the devices to trigger actions based on the signals. For example, an electrocardiography (ECG) sensor can sense the electrical activity of a user's heart over a period of time using electrodes placed on the user's body. The electrodes detect the tiny electrical changes on the skin that arise from the heart muscle depolarizing during each heartbeat. ECG recording is becoming an increasingly popular feature for wearable devices.

DETAILED DESCRIPTION

In the following detailed description, reference is made to the accompanying drawings which form a part hereof, and in which is shown by way of illustration specific examples in which the disclosure may be practiced. It is to be understood that other examples may be utilized and structural or logical changes may be made without departing from the scope of the present disclosure. The following detailed description, therefore, is not to be taken in a limiting sense, and the scope of the present disclosure is defined by the appended claims. It is to be understood that features of the various examples described herein may be combined, in part or whole, with each other, unless specifically noted otherwise.

Recording signals in wearable or Internet of Things (IoT) devices may result in high power consumption in the devices due to analog to digital (ADC) signal conversions and storage of the signals in a storage device. In addition, the longer the desired period for storing a signal, the larger the storage device needed.

Accordingly, a device (e.g., wearable device, IoT device) as described herein includes a memristor code comparator to compare a sensor signal to a reference signal. The memristor code comparator includes a memristor array including a plurality of row lines, a plurality of column lines, and a plurality of memristors, wherein each of the memristors is coupled between a unique combination of a row line and a column line. Each sensor value (i.e., digital value or analog value) of the sensor signal is applied to a corresponding row line while each corresponding reference value (i.e., digital value or analog value) of the reference signal is applied to a corresponding column line. In response to any sensor value of the sensor signal varying from a corresponding reference value of the reference signal by a threshold value, the corresponding memristor of the memristor code comparator will change states indicating the sensor signal does not match the reference signal.

If the sensor signal does not match the reference signal (i.e., an abnormal sensor signal), the abnormal sensor signal may be stored in the storage device. If the sensor signal does match the reference signal (i.e., a normal sensor signal), the normal sensor signal need not be stored in the storage device. Rather, an indicator may be stored in the storage device to indicate the sensor signal is normal. Thus, devices including a memristor code comparator to compare signals may be more power and storage efficient when only abnormal sensor signals are stored in the storage medium compared to devices in which both normal and abnormal sensor signals are stored in the storage medium. In this way, power consumption is reduced and battery life is increased.

Figure 1:
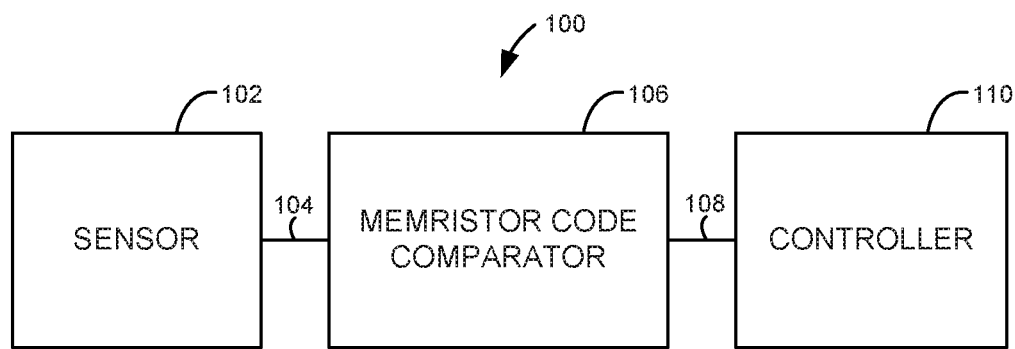
FIG. 1 is a block diagram illustrating one example of a system for comparing a sensor signal to a reference signal using a memristor code comparator.

FIG. 1 is a block diagram illustrating one example of a system 100 for comparing a sensor signal to a reference signal using a memristor code comparator. System 100 includes a sensor 102, a memristor code comparator 106, and a controller 110. Sensor 102 is communicatively coupled to memristor code comparator 106 through a communication path 104. Memristor code comparator 106 is communicatively coupled to controller 110 through a communication path 108.

In one example, system 100 is part of a wearable device or an IoT device. Sensor 102 passes a sensor signal to memristor code comparator 106. While one sensor 102 is illustrated in FIG. 1, in other examples system 100 may include multiple sensors communicatively coupled to memristor code comparator 106 such that memristor code comparator 106 receives multiple input signals from multiple sensors. In one example, sensor 102 includes an electrocardiography (ECG) sensor. In other examples, sensor 102 may include a temperature sensor, a light sensor, a sound sensor, a motion sensor, a touch sensor, or another suitable sensor.

Sensor 102 may be a digital sensor to provide a digital sensor signal or an analog sensor to provide an analog sensor signal. A digital sensor signal may include multiple bits with each bit passed to a corresponding input of memristor code comparator 106. In one example, an analog sensor signal may include a single analog signal, which is passed to a single input of memristor code comparator 106. In another example, a single analog sensor signal may be represented by a plurality of analog sensor values with each of the plurality of analog sensor values representing the single analog sensor signal at a different point in time. In this example, each of the plurality of analog sensor values are passed to a corresponding input of memristor code comparator 106.

As will be described in more detail below with reference to FIG. 2, memristor code comparator 106 includes a memristor array including a plurality of row lines, a plurality of column lines, and a plurality of memristors, wherein each of the memristors is coupled between a unique combination of a row line and a column line. Memristor code comparator 106 compares a sensor signal received from sensor 102 to a reference signal. Controller 110 determines a status of the sensor signal based on the comparison. In one example, controller 110 writes the sensor signal to a storage medium in response to determining the status of the sensor signal is abnormal.

Figure 2:
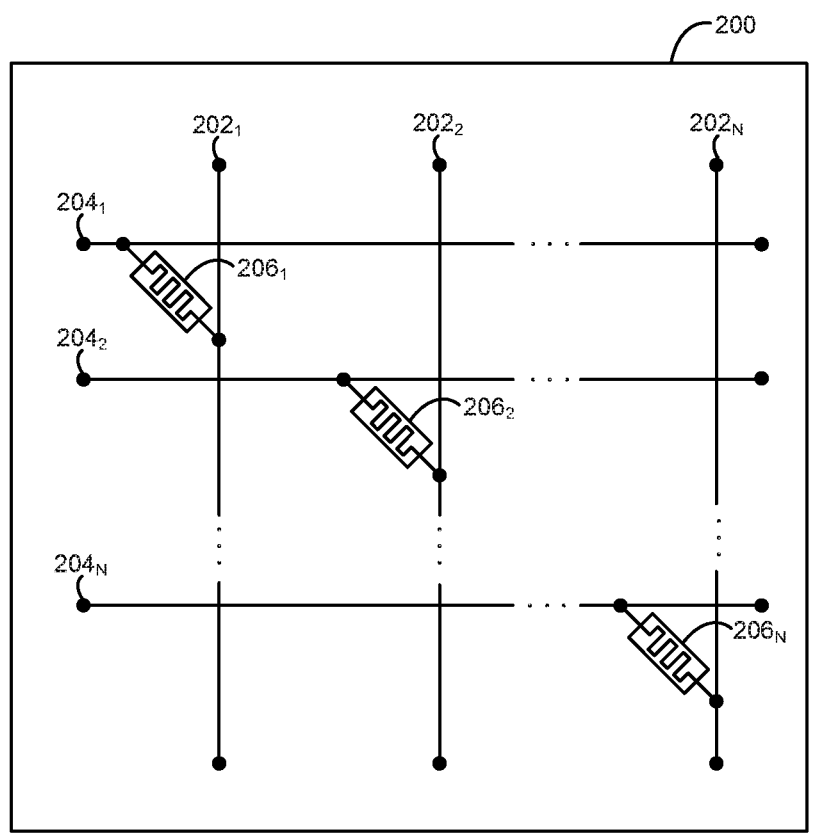
FIG. 2 illustrates one example of a memristor code comparator.

FIG. 2 illustrates one example of a core circuit of memristor code comparator 200. In one example, memristor code comparator 200 provides memristor code comparator 106 previously described and illustrated with reference to FIG. 1. Memristor code comparator 200 includes a plurality of column lines $202_1$ through $202_N$, a plurality of row lines $204_1$ through $204_N$, and a plurality of memristors $206_1$ through $206_N$, where "N" is any suitable number based on the number of bits (for digital sensor signals) or the number of analog values (for analog sensor signals) to be compared. A first terminal of each memristor $206_1$ through $206_N$ is electrically coupled to a column line $202_1$ through $202_N$ and a second terminal of each memristor $206_1$ through $206_N$ is electrically coupled to a row line $204_1$ through $204_N$, respectively.

Memristors $206_1$ through $206_N$ are two-terminal passive devices that can be electrically switched between two states including a high-resistance state (HRS) and a low-resistance state (LRS). The switching event from a HRS to a LRS is called a "Set" or "On" switching process. Conversely, the switching from a LRS to a HRS is called a "Reset" or "Off" switching process. Based on the electrical switching conditions, memristors can be classified into two categories including bipolar memristors and unipolar (or nonpolar) memristors. Bipolar memristors are switched by using one voltage polarity for Set switching and the opposite voltage polarity for Reset switching. In contrast, unipolar memristors may be switched by using the same voltage polarity for both the Set and Reset switching. In one example, memristors $206_1$ through $206_N$ are unipolar memristors. The desired unipolar memristor for a code comparator exhibits symmetrical Set switching with respect to voltage polarity, desired switching threshold voltage, low switching current, high off/on resistance ratio, consistent LRS with small variation, and reasonable endurance. The large off/on resistance ratio increases the signal to noise ratio (SNR) by suppressing the background Off current and enables a larger comparator size for comparison. Memristors may be tuned by device engineering (e.g., via setting of oxide thickness, device size, material composition selection, etc.) to provide the desired performance including the switching voltage threshold and switching current.

To Reset a unipolar memristor from the LRS to the HRS, a voltage is applied across the memristor with no current compliance. The resistance change occurs when the current through the memristor becomes larger than the value of the compliance. To Set the unipolar memristor from the HRS to the LRS, a voltage with current compliance is applied across the memristor. The resistance change occurs when the voltage across the memristor exceeds a threshold voltage of the memristor.

Prior to comparing a sensor signal to a reference signal, each memristor $206_1$ through $206_N$ is Reset to the HRS. A memristor $206_1$ through $206_N$ may be Reset to the HRS by applying an appropriate voltage without current compliance between the corresponding column line $202_1$ through $202_N$ and row line $204_1$ through $204_N$ for the memristor, respectively. With each memristor $206_1$ through $206_N$ in the HRS, a reference signal is applied to column lines $202_1$ through $202_N$ and a sensor signal is applied to row lines $204_1$ through $204_N$.

A digital sensor signal may include multiple bits with each bit passed to a corresponding row line $204_1$ through $204_N$. In this case, a corresponding digital reference signal includes multiple bits with each bit passed to a corresponding column line $202_1$ through $202_N$. In one example, an analog sensor signal may include a single analog signal, which is passed to a single row line. In this case, a corresponding analog sensor signal is applied to the corresponding column line. In another example, a single analog sensor signal may be represented by a plurality of analog sensor values with each of the plurality of analog sensor values representing the single analog sensor signal at a different point in time. In this example, each of the plurality of analog sensor values is passed to a corresponding row line $204_1$ through $204_N$. In this case, a corresponding plurality of analog reference values representing a single analog reference signal at different points in time is applied to column lines $202_1$ through $202_N$.

In response to each sensor value on each row line matching the corresponding reference value on the corresponding column line within a threshold value (i.e., the voltage on each row line equals the voltage on the corresponding column line such that the threshold voltage of each corresponding memristor is not exceeded), the corresponding memristor remains in the HRS. In response to a sensor value on a row line differing from the corresponding reference value on the corresponding column line by the threshold value (i.e., the voltage on a row line does not equal the voltage on the corresponding column line such that the threshold voltage of the corresponding memristor is exceeded), the corresponding memristor switches to the LRS.

The reference values and the sensor values are then removed from column lines $202_1$ through $202_N$ and row lines $204_1$ through $204_N$, respectively. Memristors $206_1$ through $206_N$ are then read to determine if any of the memristors have been switched to the LRS. Memristor $206_1$ through $206_N$ may be read by grounding one end of each column line $202_1$ through $202_N$ and applying a read voltage to each row line $204_1$ through $204_N$. The current through the other end of each column line $202_1$ through $202_N$ may be summed to provide an indication of how many (if any) of memristors $206_1$ through $206_N$ have been switched to the LRS. If none of the memristors $206_1$ through $206_N$ have been switched to the LRS, the summed current will be a minimum value. Any memristors $206_1$ through $206_N$ that have been switched to the LRS may then be Reset to the HRS and the process may be repeated for the next comparison of the sensor signal to the reference signal.

Figure 3:
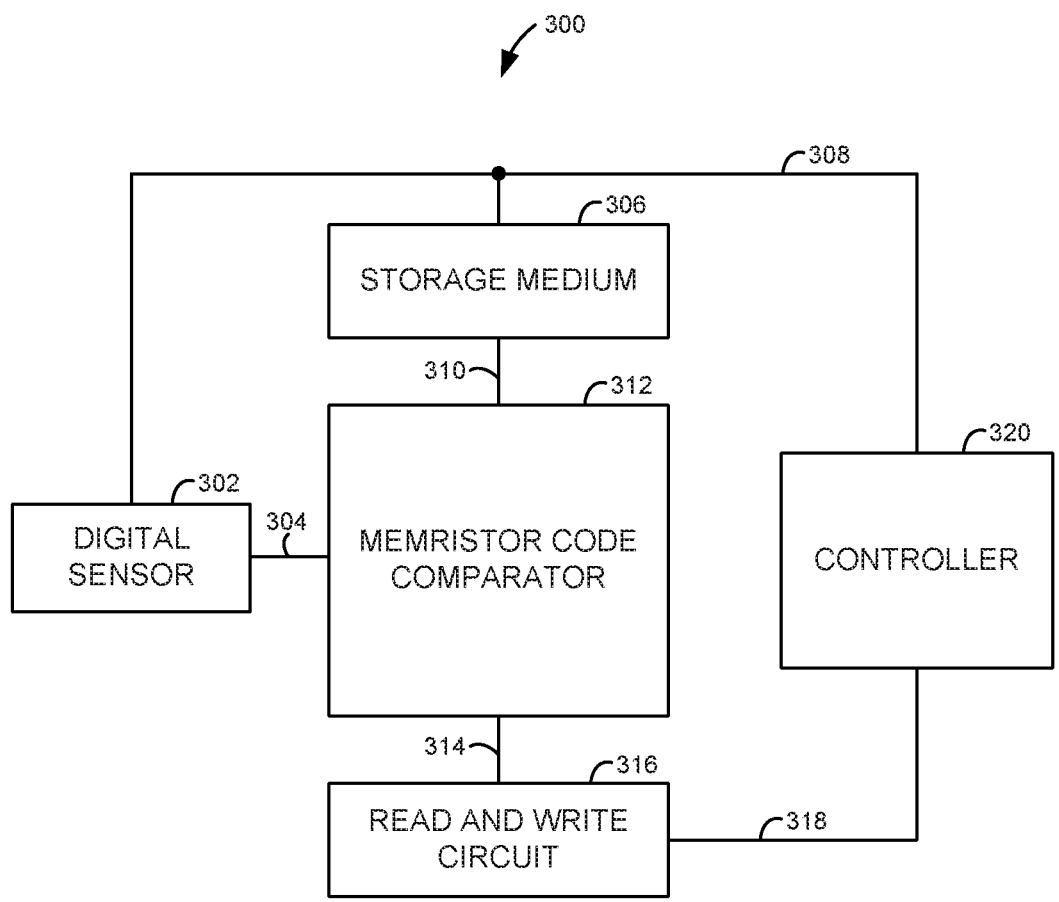
FIG. 3 is a block diagram illustrating one example of a system for comparing a digital sensor signal to a digital reference signal using a memristor code comparator.

FIG. 3 is a block diagram illustrating one example of a system 300 for comparing a digital sensor signal to a digital reference signal using a memristor code comparator. In one example, system 300 is part of a wearable device or an IoT device. System 300 includes a digital sensor 302, a storage medium 306, a memristor code comparator 312, a read and write circuit 316, and a controller 320. Digital sensor 302 is communicatively coupled to memristor code comparator 312 through a communication path 304 and to storage medium 306 and controller 320 through a communication path 308. Storage medium 306 is communicatively coupled to memristor code comparator 312 through a communication path 310. Memristor code comparator 312 is communicatively coupled to read and write circuit 316 through a communication path 314. Read and write circuit 316 is communicatively coupled to controller 320 through a communication path 318.

Digital sensor 302 provides a multibit digital sensor signal to memristor code comparator 312 such that each bit of the digital sensor signal is passed to a corresponding row of memristor code comparator 312. Storage medium 306 is a machine-readable storage medium. Storage medium 306 may be any suitable electronic, magnetic, optical, or other physical storage device that stores data and/or executable instructions. Thus, storage medium 306 may be, for example, a random access memory (RAM), an electrically-erasable programmable read-only memory (EEPROM), a storage drive, a flash drive, a register, and the like. Storage medium 306 passes a multibit digital reference signal to memristor code comparator 312 such that each bit of the digital reference signal is passed to a corresponding column of memristor code comparator 312. In one example, the digital reference signal may be predefined and stored in storage medium 306 by a device external to system 300. In another example, the digital reference signal may be derived from a digital sensor signal provided by digital sensor 302 known to be the desired (i.e., normal) signal and then stored in storage medium 306 by system 300.

Memristor code comparator 312 is similar to memristor code comparator 200 previously described and illustrated with reference to FIG. 2. Memristor code comparator 312 compares the digital sensor signal received from digital sensor 302 to the digital reference signal received from storage medium 306. Read and write circuit 316 reads the state of the memristors of memristor code comparator 312 after each comparison. In response to reading that at least one memristor has changed states, read and write circuit 316 passes a "no match" or "abnormal" indicator to controller 320. In response to reading that no memristors have changed states, read and write circuit 316 passes a "match" or "normal" indicator to controller 320. Read and write circuit 316 then writes each memristor that changed states (e.g., from the HRS to the LRS) during the comparison back to the initial state (e.g., from the LRS to the HRS) prior to performing the next comparison of the digital sensor signal to the digital reference signal.

Controller 320 controls the operation of system 300 including the timing of signals passed to memristor code comparator 312 from digital sensor 302 and storage medium 306 and the reading and writing of memristors within memristor code comparator 312 by read and write circuit 316. Controller 320 may include a processor, a microcontroller, an application-specific integrated circuit (ASIC), a field-programmable gate array (FPGA), or other suitable logic circuitry. In one example, controller 320 retrieves and executes instructions stored in storage medium 306 to control the operation of system 300.

Controller 320 may trigger an action in response to read and write circuit 316 indicating that a memristor changed states during the comparison indicating the sensor signal does not match the reference signal. In one example in response to the sensor signal not matching the reference signal, controller 320 writes the non-matching digital sensor signal to storage medium 306. In another example in response to the sensor signal not matching the reference signal, controller 320 triggers an alert, such as an audible alert, a visual alert, or a haptic alert of system 300. In response to the sensor signal matching the reference signal, controller 320 may store an indicator to storage medium 306 indicating the reference signal matched the reference signal.

Figure 4:
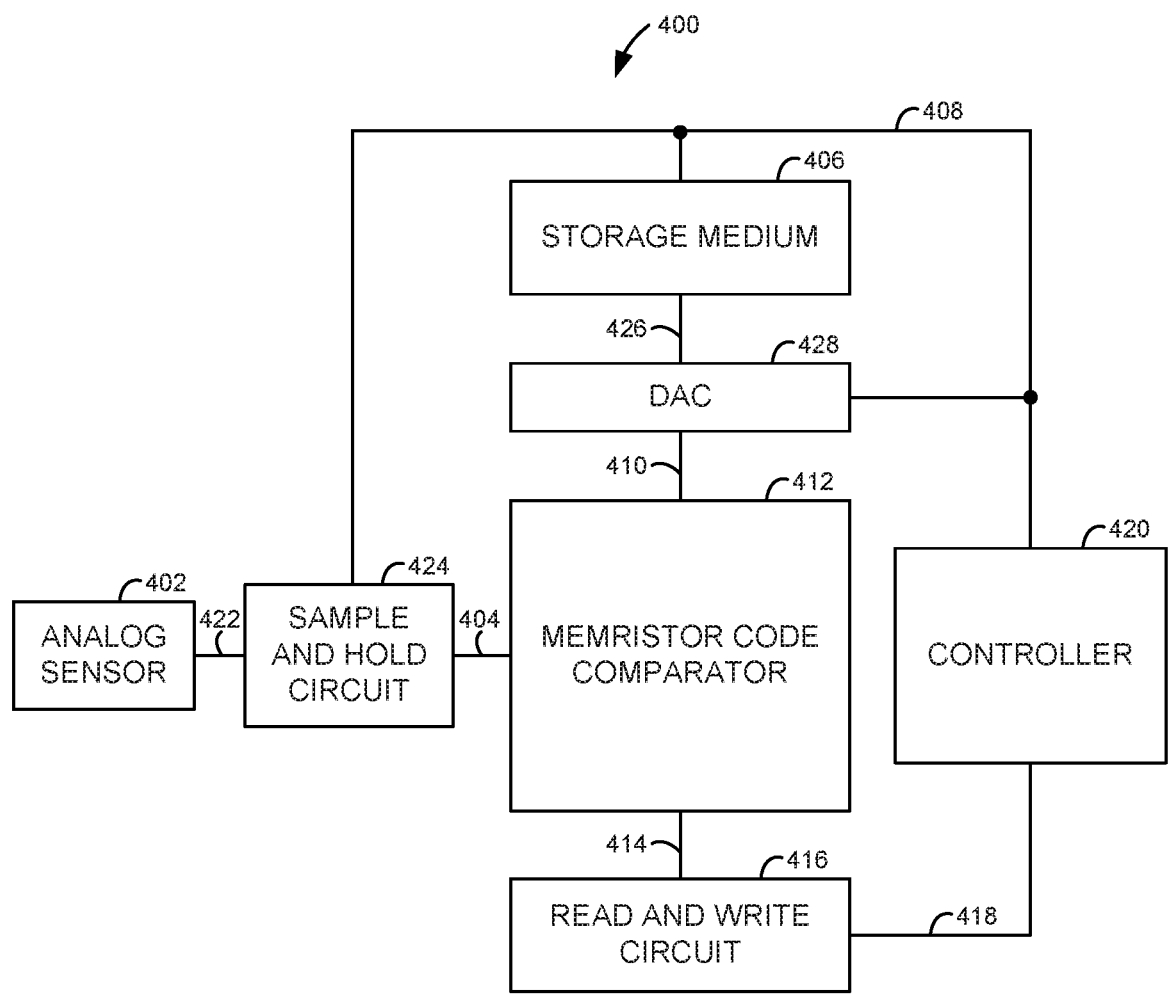
FIG. 4 is a block diagram illustrating one example of a system for comparing an analog sensor signal to an analog reference signal using a memristor code comparator.

FIG. 4 is a block diagram illustrating one example of a system 400 for comparing an analog sensor signal to an analog reference signal using a memristor code comparator. In one example, system 400 is part of a wearable device or an IoT device. System 400 includes an analog sensor 402, a sample and hold circuit 424, a storage medium 406, a digital to analog convertor (DAC) 428, a memristor code comparator 412, a read and write circuit 416, and a controller 420. Analog sensor 402 is communicatively coupled to sample and hold circuit 424 through a communication path 422. Sample and hold circuit 424 is communicatively coupled to memristor code comparator 412 through a communication path 404 and to storage medium 406, DAC 428, and controller 420 through a communication path 408. Storage medium 406 is communicatively coupled to DAC 428 through a communication path 426. DAC 428 is communicatively coupled to memristor code comparator 412 through a communication path 410. Memristor code comparator 412 is communicatively coupled to read and write circuit 416 through a communication path 414. Read and write circuit 416 is communicatively coupled to controller 420 through a communication path 418. In one example, system 400 may also include an amplifier circuit (not shown) between sample and hold circuit 424 and memristor code comparator 412. The amplifier circuit may be used to amplify signals from sample and hold circuit 424 if analog sensor 402 provides an analog signal that would be too small for memristor switching within memristor code comparator 412.

Analog sensor 402 provides at least one analog sensor signal to sample and hold circuit 424. In other examples, multiple analog sensors may be used to provide a plurality of analog sensor signals to sample and hold circuit 424. In one example, analog sensor 402 is an ECG sensor or another suitable sensor.

In one example, sample and hold circuit 424 receives a plurality of analog sensor signals and samples and holds each analog sensor signal to provide corresponding analog sensor values to corresponding rows of memristor code comparator 412. In another example, sample and hold circuit 424 receives a single analog sensor signal and samples and holds the single analog sensor signal over time to simultaneously provide a plurality of analog sensor values representing the single analog sensor signal at different points in time to corresponding rows of memristor code comparator 412.

Storage medium 406 is a machine-readable storage medium. Storage medium 406 may be any suitable electronic, magnetic, optical, or other physical storage device that stores data and/or executable instructions. Thus, storage medium 406 may be, for example, a RAM, an EEPROM, a storage drive, a flash drive, a register, and the like. In one example in which sample and hold circuit 424 receives a plurality of analog sensor signals, storage medium 406 passes a corresponding digital reference signal for each analog sensor signal to DAC 428. DAC 428 converts each digital reference signal to provide corresponding analog reference values, which are passed to corresponding columns of memristor code comparator 412.

In another example in which sample and hold circuit 424 receives a single analog sensor signal to provide a plurality of analog sensor values representing the single analog sensor signal at different points in time, storage medium 406 passes corresponding digital reference values for each analog sensor value to DAC 428. DAC 428 converts the digital reference values to corresponding analog reference values, which are passed to corresponding columns of memristor code comparator 412. In one example, the digital reference values may be predefined and stored in storage medium 406 by a device external to system 400. In another example, the digital reference values may be derived from an analog sensor signal provided by analog sensor 402 known to be the desired (i.e., normal) signal.

Memristor code comparator 412 is similar to memristor code comparator 200 previously described and illustrated with reference to FIG. 2. Memristor code comparator 412 compares the analog sensor values received from sample and hold circuit 424 to the analog reference values received from DAC 428. Read and write circuit 416 reads the state of the memristors of memristor code comparator 412 after each comparison. In response to reading that at least one memristor has changed states, read and write circuit 416 passes a "no match" or "abnormal" indicator to controller 420. In response to reading that no memristors have changed states, read and write circuit 416 passes a "match" or "normal" indicator to controller 420. Read and write circuit 416 then writes each memristor that changed states (e.g., from the HRS to the LRS) during the comparison back to the initial state (e.g., from the LRS to the HRS) prior to performing the next comparison of analog sensor values to analog reference values.

Controller 420 controls the operation of system 400 including the timing of signals passed to memristor code comparator 412 from sample and hold circuit 424 and DAC 428 and the reading and writing of memristors within memristor code comparator 412 by read and write circuit 416. Controller 420 may include a processor, a microcontroller, an ASIC, or other suitable logic circuitry. In one example, controller 420 retrieves and executes instructions stored in storage medium 406 to control the operation of system 400.

Controller 420 may trigger an action in response to read and write circuit 416 indicating that a memristor changed states during the comparison indicating the sensor signal does not match the reference signal. In one example in response to the sensor signal not matching the reference signal, controller 420 converts the non-matching analog sensor signal to a digital signal and writes the digital signal to storage medium 406. In another example in response to the sensor signal not matching the reference signal, controller 420 triggers an alert, such as an audible alert, a visual alert, or a haptic alert of system 400. In response to the sensor signal matching the reference signal, controller 420 may store an indicator to storage medium 406 indicating the reference signal matched the reference signal.

Figure 5:
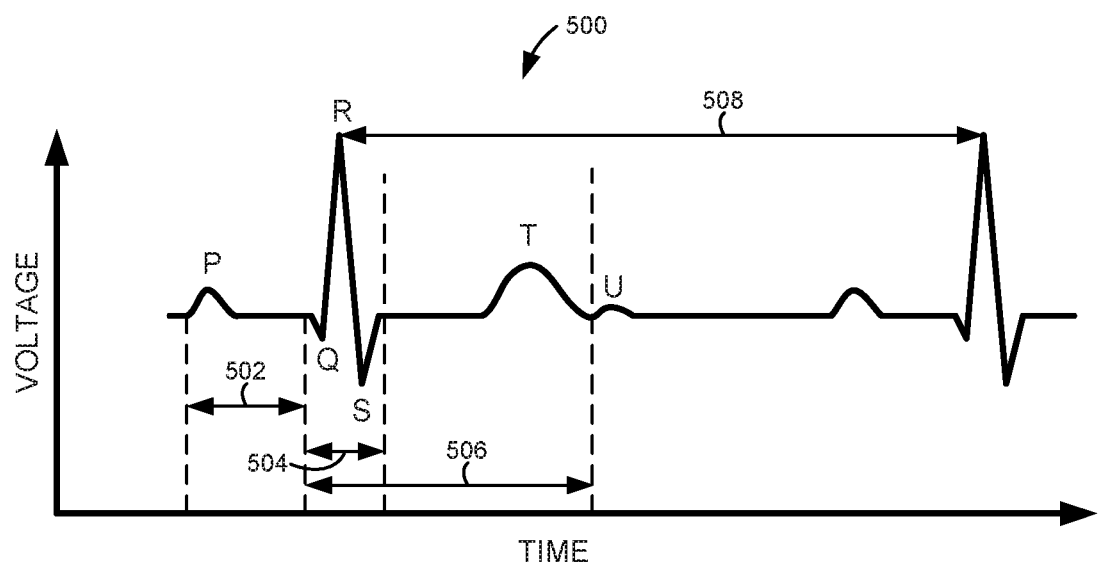
FIG. 5 illustrates one example of an electrocardiography (ECG) sensor signal.

FIG. 5 illustrates one example of an ECG sensor signal 500. ECG sensor signal 500 may be provided by an ECG sensor, such as by an analog sensor 402 of system 400 previously described and illustrated with reference to FIG. 4. For an ECG sensor, an amplifier circuit may be used between sample and hold circuit 424 and memristor code comparator 412 to amplify the signal (e.g., the signal voltage peak to peak amplified from 0.5 mV to 2 V). ECG sensor signal 500 includes features P, Q, R, S, T, and U, which repeat for each heartbeat of a user. A normal ECG sensor signal has a PQ interval as indicated at 502 between about 0.12 and 0.20 seconds, a QRS duration as indicated at 504 between about 0.08 and 0.10 seconds, a QT interval as indicated at 506 between about 0.40 and 0.43 seconds, and a RR interval as indicated at 508 between about 0.6 and 1.0 seconds.

Different points of ECG sensor signal 500 may be sampled and held to simultaneously provide a plurality of analog sensor values representing ECG sensor signal 500 at different points in time. For example, a sample and hold circuit may provide a first analog sensor value for point P, a second analog sensor value for point Q, a third analog sensor value for point R, a fourth analog sensor value for point S, a fifth analog sensor value for point T, and a sixth analog sensor value for point U. Additional analog sensor values at other points may also be provided. The sample and hold circuit may provide each of the first through sixth analog sensor values to a memristor code comparator simultaneously such that the shape of ECG sensor signal 500 may be compared to an ECG reference signal shape using a single comparison by the memristor code comparator.

Figure 6:
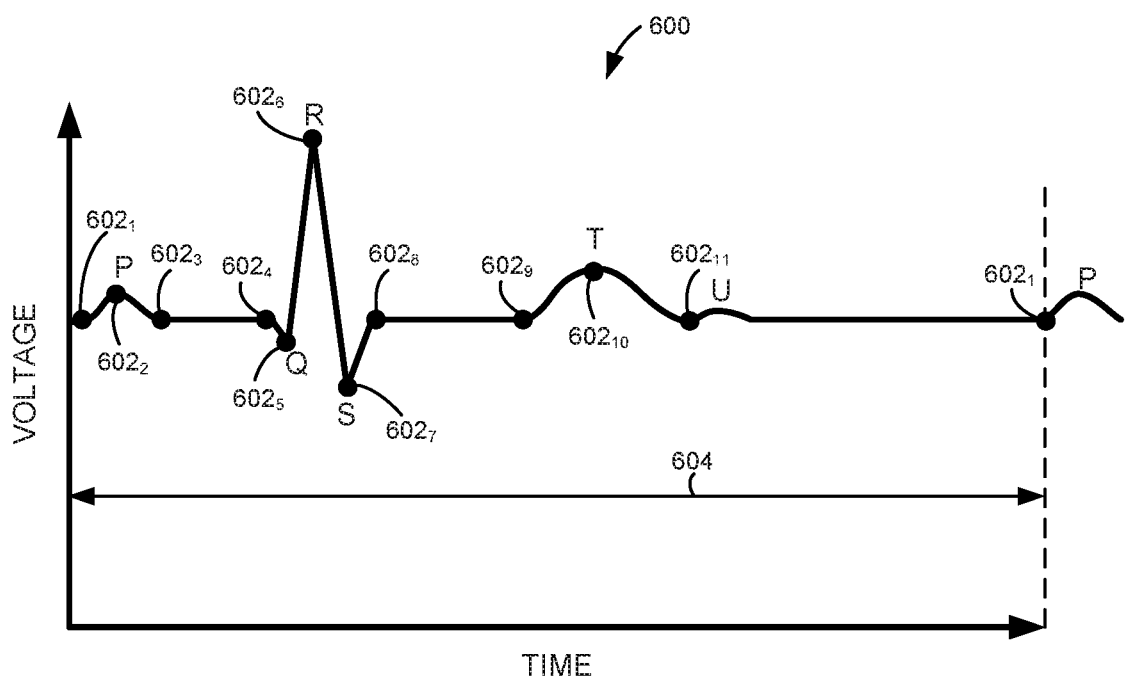
FIG. 6 illustrates one example of an ECG reference signal.

FIG. 6 illustrates one example of an ECG reference signal 600. In one example, ECG reference signal 600 is a standard normalized ECG reference signal based on a user's ECG sensor signal, such as ECG sensor signal 500 previously described and illustrated with reference to FIG. 5. One P-P cycle, as indicated at 604, may be used as the reference signal. Accordingly, by comparing one P-P cycle of ECG reference signal 600 to a P-P cycle of ECG sensor signal 500, an abnormal ECG sensor signal can be detected.

ECG reference signal 600 may be stored in a storage medium as an array of voltage values with reference to time and/or pattern. For example, the array of voltage values <0.1 mV, 0.5 mV, 0.1 mV, 0.1 mV, 0 mV, 2 mV, −0.1 mV, 0.1 mV, 0.1 mV, 1 mV, 0.1 mV> corresponding to points 6021 through 60211, respectively, may be used as reference values to compare to the corresponding points in time of ECG sensor signal 500. The reference values (i.e., voltages) are passed to the corresponding columns of the memristor code comparator.

The sample and hold circuit samples and holds the corresponding sensor values (i.e., voltages) at the corresponding points in time of the ECG sensor signal and passes the sensor values to the corresponding rows of the memristor code comparator. The memristor code comparator may then compare the ECG sensor values to the ECG reference values to determine if the ECG sensor signal varies from the ECG reference signal. In one example, the ECG sensor signal is compared to the ECG reference signal for each heartbeat. In other examples, the ECG sensor signal is compared to the ECG reference signal once for each of a plurality of heartbeats, such as every other heartbeat, every third heartbeat, every fourth heartbeat, etc.

Figure 7:
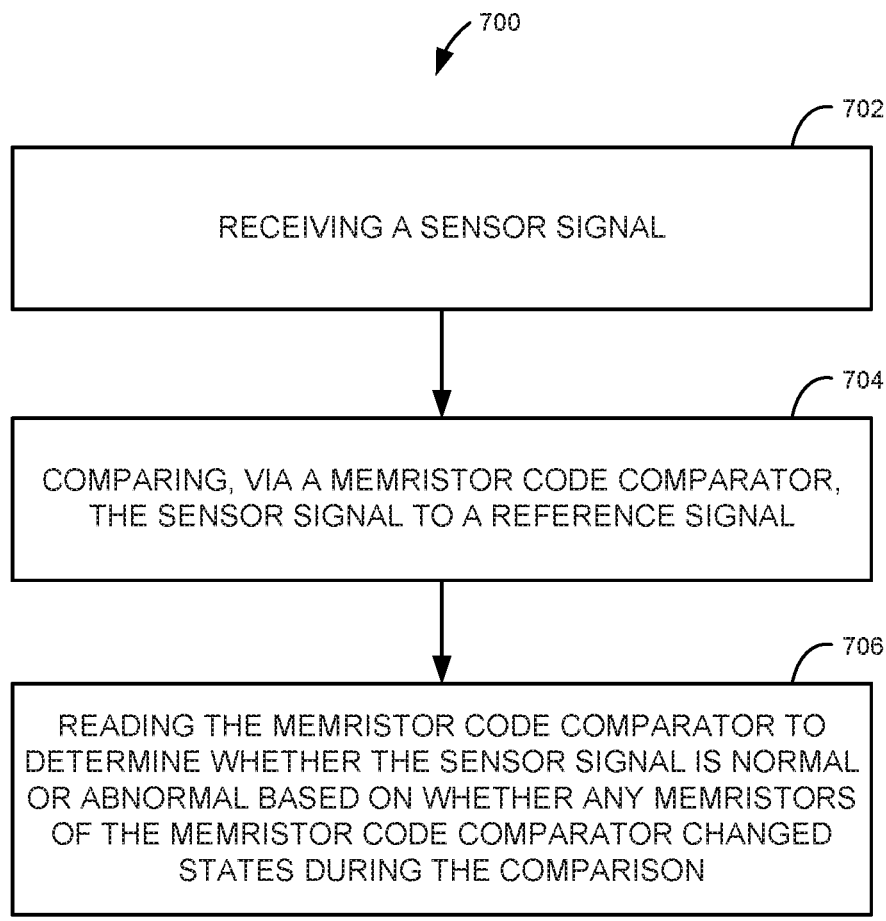
FIG. 7 is a flow diagram illustrating one example of a method for comparing a sensor signal to a reference signal using a memristor code comparator.

FIG. 7 is a flow diagram illustrating one example of a method 700 for comparing a sensor signal to a reference signal using a memristor code comparator. At 702, method 700 includes receiving a sensor signal. In one example, receiving the sensor signal includes receiving an ECG signal from an ECG sensor of a wearable device. At 704, method 700 includes comparing, via a memristor code comparator, the sensor signal to a reference signal. At 706, method 700 includes reading the memristor code comparator to determine whether the sensor signal is normal or abnormal based on whether any memristors of the memristor code comparator changed states during the comparison.

In one example, comparing, via the memristor code comparator, the sensor signal to the reference signal includes changing the state of a corresponding memristor of the memristor code comparator in response to a voltage difference between a corresponding value of the sensor signal and a corresponding value of the reference signal exceeding a threshold value of the corresponding memristor. Method 700 may further include resetting memristors of the memristor code comparator to an initial state in response to memristors of the memristor code comparator changing states during the comparison. Method 700 may also include storing the sensor signal to a storage medium in response to determining the sensor signal is abnormal and storing an indicator to the storage medium indicating the sensor signal is normal in response to determining the sensor signal is normal.

Although specific examples have been illustrated and described herein, a variety of alternate and/or equivalent implementations may be substituted for the specific examples shown and described without departing from the scope of the present disclosure. This application is intended to cover any adaptations or variations of the specific examples discussed herein. Therefore, it is intended that this disclosure be limited only by the claims and the equivalents thereof.

The invention claimed is:

1. A device comprising:
a sensor to provide a sensor signal;
a memristor code comparator to compare the sensor signal to a reference signal;
a read and write circuit to read the state of the memristors of the memristor code comparator after each comparison and to write each memristor that changed states during the comparison back to an initial state; and
a controller to determine a status of the sensor signal based on the comparison.

2. The device of claim 1, wherein the memristor code comparator comprises a plurality of row lines, a plurality of column lines, and a plurality of unipolar memristors, wherein each of the memristors is coupled between a row line and a column line.

3. The device of claim 1, wherein the controller is to write the sensor signal to a storage medium in response to determining the status of the sensor signal is abnormal.

4. The device of claim 1, wherein the sensor provides an analog sensor signal.

5. The device of claim 1, wherein the sensor comprises an electrocardiography (ECG) sensor.

6. A device comprising:
a sensor to provide a sensor signal;
a storage medium storing a reference signal;
a memristor code comparator to compare the sensor signal to the reference signal;
a read and write circuit to read the state of the memristors of the memristor code comparator after each comparison and to write each memristor that changed states during the comparison back to an initial state; and
a controller to trigger an action in response to a memristor changing states during the comparison indicating the sensor signal does not match the reference signal.

7. The device of claim 6, further comprising:
a sample and hold circuit to receive the sensor signal from the sensor and provide a plurality of analog sensor values representative of the sensor signal at different points in time to the memristor code comparator; and
a digital to analog converter to convert a plurality of digital reference values stored in the storage medium to provide a plurality of analog reference values representative of the reference signal at the different points in time to the memristor code comparator.

8. The device of claim 6, wherein the sensor signal comprises a multibit digital sensor signal, and
wherein the reference signal comprises a multibit digital reference signal.

9. The device of claim 6, wherein the memristor code comparator comprises a memristor array comprising a plurality of row lines, a plurality of column lines, and a plurality of memristors, wherein each of the memristors is coupled between a unique combination of a row line and a column line,
wherein the sensor signal is applied to the row lines, and wherein the reference signal is applied to the column lines.

10. The device of claim 6, wherein the sensor signal comprises an electrocardiography (ECG) signal, and
wherein the reference signal comprises a standard normalized ECG reference signal.

11. A method comprising:
receiving a sensor signal;
comparing, via a memristor code comparator, the sensor signal to a reference signal; and
reading the memristor code comparator to determine whether the sensor signal is normal or abnormal based on whether any memristors of the memristor code comparator changed states during the comparison,
wherein comparing, via the memristor code comparator, the sensor signal to the reference signal comprises changing the state of a corresponding memristor of the memristor code comparator in response to a voltage difference between a corresponding value of the sensor signal and a corresponding value of the reference signal exceeding a threshold value of the corresponding memristor.

12. A method comprising:
receiving a sensor signal;
comparing, via a memristor code comparator, the sensor signal to a reference signal;
reading the memristor code comparator to determine whether the sensor signal is normal or abnormal based on whether any memristors of the memristor code comparator changed states during the comparison; and
resetting memristors of the memristor code comparator to an initial state in response to memristors of the memristor code comparator changing states during the comparison.

13. The method of claim 12, further comprising:
storing the sensor signal to a storage medium in response to determining the sensor signal is abnormal; and
storing an indicator to the storage medium indicating the sensor signal is normal in response to determining the sensor signal is normal.

14. The method of claim 12, wherein receiving a sensor signal comprises receiving an electrocardiography (ECG) signal from an ECG sensor of a wearable device.

15. The method of claim 12, wherein receiving the sensor signal comprises receiving an analog sensor signal.

16. The method of claim 11, further comprising:
storing the sensor signal to a storage medium in response to determining the sensor signal is abnormal; and
storing an indicator to the storage medium indicating the sensor signal is normal in response to determining the sensor signal is normal.

17. The method of claim 11, wherein receiving a sensor signal comprises receiving an electrocardiography (ECG) signal from an ECG sensor of a wearable device.

18. The method of claim 11, wherein receiving the sensor signal comprises receiving an analog sensor signal.

19. The device of claim 1, further comprising:
a sample and hold circuit to receive the sensor signal from the sensor and provide a plurality of analog sensor values representative of the sensor signal at different points in time to the memristor code comparator; and
a digital to analog converter to convert a plurality of digital reference values to provide a plurality of analog reference values representative of the reference signal at the different points in time to the memristor code comparator.

20. The device of claim 1, wherein the sensor signal comprises a multibit digital sensor signal, and
wherein the reference signal comprises a multibit digital reference signal.

* * * * *